United States Patent [19]

Tapley

[11] Patent Number: 5,366,660
[45] Date of Patent: Nov. 22, 1994

[54] DISPERSIONS

[75] Inventor: Carole A. M. Tapley, Stockton on Tees, England

[73] Assignee: Tioxide Specialties Limited, London, England

[21] Appl. No.: 953,219

[22] Filed: Sep. 30, 1992

[30] Foreign Application Priority Data

Oct. 4, 1991 [GB] United Kingdom ............. 9121143.3

[51] Int. Cl.$^5$ .................. B01J 13/00; A61K 7/42; C09C 1/04; G02B 5/23
[52] U.S. Cl. .................. 252/309; 106/425; 106/426; 252/314; 252/588; 424/59
[58] Field of Search .............. 252/309, 314, 588; 424/59, 642; 106/425, 426

[56] References Cited

U.S. PATENT DOCUMENTS

| | | | |
|---|---|---|---|
| Re. 27,818 | 11/1973 | Werner | 106/437 |
| 2,296,636 | 9/1942 | Hanahan | 106/420 |
| 2,387,534 | 10/1945 | Seidel | 106/442 |
| 2,671,758 | 3/1954 | Vinograd et al. | 252/309 X |
| 2,885,366 | 5/1959 | Iler | 252/313.2 |
| 3,298,959 | 1/1967 | Marks et al. | 252/588 |
| 3,409,560 | 11/1968 | Faust et al. | 252/309 |
| 3,410,708 | 11/1968 | McGinnis | 106/437 |
| 3,437,502 | 4/1969 | Werner | 106/437 |
| 3,579,310 | 5/1971 | Lewis et al. | 23/301 |
| 3,591,398 | 6/1971 | Angerman | 106/444 |
| 3,676,342 | 7/1972 | Gathman et al. | 252/309 X |
| 3,728,443 | 4/1973 | Berisford et al. | 423/610 |
| 3,907,581 | 9/1975 | Willcox | 106/187 |
| 3,923,968 | 12/1975 | Basque et al. | 423/611 |
| 3,928,057 | 12/1975 | Decolibus | 106/446 |
| 3,954,496 | 5/1976 | Batzar | 106/404 |
| 3,960,589 | 6/1976 | Morrison et al. | 106/425 |
| 4,075,031 | 2/1978 | Allen | 106/446 |
| 4,199,370 | 4/1980 | Brand | 106/446 |
| 4,923,518 | 5/1990 | Brand et al. | 106/429 |

FOREIGN PATENT DOCUMENTS

| | | |
|---|---|---|
| 0073340 | 7/1982 | European Pat. Off. |
| 0214308 | 3/1986 | European Pat. Off. |
| 0433086 | 6/1991 | European Pat. Off. |
| 2740561 | 3/1978 | Germany |
| 49-000450 | 1/1974 | Japan |
| 52-072833 | 6/1977 | Japan |
| 53-124627 | 10/1978 | Japan |
| 54-073139 | 6/1979 | Japan |
| 55-154317 | 12/1980 | Japan |
| 58-043912 | 3/1983 | Japan |
| 58-062106 | 4/1983 | Japan |
| 59-015885 | 4/1984 | Japan |
| 59-062517 | 4/1984 | Japan |
| 57067681 | 4/1984 | Japan |
| 59-098009 | 6/1984 | Japan |
| 59-172415 | 9/1984 | Japan |
| 59-223231 | 12/1984 | Japan |

(List continued on next page.)

OTHER PUBLICATIONS

"Paints for the skin coloring", Hirosawa, Akio et al., Chemical Abstracts, vol. 87, p. 300, 1977.

*Primary Examiner*—Richard D. Lovering
*Attorney, Agent, or Firm*—Baker & Botts

[57] ABSTRACT

An oil dispersion which is substantially transparent to visible light comprises an oil, particles of zinc oxide having an average size of from 0.005 to 0.15 micron and an organic dispersing agent. The solids content of the dispersion is at least 30 weight percent, its extinction coefficients at 308 nm (E(308)) and 360 nm (E(360)) wavelengths are both at least 9 liters per gram per centimeter and the ratio E(360):E(308) is in the range 0.75:1 to 1.5:1.

A method of preparing the dispersion is also described in which the ingredients are milled together in the presence of a particulate grinding medium until the required particle size and optical properties are obtained.

The dispersions are useful in sun-screening preparations and especially those products designed to provide a balanced protection from UVA and UVB radiation.

29 Claims, No Drawings

FOREIGN PATENT DOCUMENTS

| Number | Date | Country |
|---|---|---|
| 60-186418 | 9/1985 | Japan . |
| 60-231607 | 11/1985 | Japan . |
| 62260716 | 11/1985 | Japan . |
| 61-037711 | 2/1986 | Japan . |
| 61-097133 | 5/1986 | Japan . |
| 61-215216 | 9/1986 | Japan . |
| 62-040292 | 8/1987 | Japan . |
| 63-072620 | 4/1988 | Japan . |
| 63-132821 | 6/1988 | Japan . |
| 2208369 | 8/1990 | Japan . |
| 2212414 | 8/1990 | Japan . |
| 2289506 | 11/1990 | Japan . |
| 3134069 | 6/1991 | Japan . |
| 3183620 | 8/1991 | Japan . |
| 3199121 | 8/1991 | Japan . |
| 1109369 | 12/1965 | United Kingdom . |
| 1256341 | 12/1971 | United Kingdom . |
| 1387281 | 3/1975 | United Kingdom . |
| 1541621 | 5/1976 | United Kingdom . |
| 1479988 | 7/1977 | United Kingdom . |
| 1500600 | 2/1978 | United Kingdom . |
| 2108097 | 9/1982 | United Kingdom . |
| 2184356 | 6/1987 | United Kingdom . |
| 2205088 | 5/1988 | United Kingdom . |
| 2206339 | 1/1989 | United Kingdom . |
| 2226018 | 11/1989 | United Kingdom . |
| 458535 | 3/1975 | U.S.S.R. . |
| WO9213517 | 8/1992 | WIPO . |

DISPERSIONS

This invention relates to dispersions of zinc oxide particles and particularly to dispersions of these particles in an oil.

According to the present invention an oil dispersion comprises an oil, particles of zinc oxide having an average size of from 0.005 to 0.15 micron and an organic dispersing agent for said particles, the amount of said particles being such that the dispersion has a solids content of greater than 30 percent by weight and said dispersion being substantially transparent to visible light and having an absorbance for ultraviolet light such that the extinction coefficient (E(308)) at a wavelength of 308 nm is at least 9 liters per gram per centimeter, the extinction coefficient (E(360)) at a wavelength of 360 nm is at least 9 liters per gram percentimeter and the ratio E(360):E(308) is in the range 0.75:1 to 1.5:1.

According to the invention also a method for the manufacture of an oil dispersion comprises milling particulate zinc oxide in an oil in the presence of a particulate grinding medium and an organic dispersing agent for said zinc oxide in said oil in which the amount of zinc oxide is such that the dispersion has a solids content of greater than 30 percent by weight and continuing said milling for a period of time such that the particulate zinc oxide has an average size of from 0.005 to 0.15 micron and that the dispersion obtained is substantially transparent to visible light and has an absorbance for ultraviolet light such that the extinction coefficient (E(308)) at a wavelength of 308 nm is at least 9 liters per gram per centimeter, the extinction coefficient (E(360)) at a wavelength of 360 nm is at least 9 liters per gram per centimeter and the ratio E(360):E(308) is in the range 0.75:1 to 1.5:1.

It is preferred that the dispersions of the current invention have a high solids content since this enables the dispersions to be used in a wide range of final products. Particularly useful dispersions are those in which the solids content is at least 40 percent by weight and dispersions in which the solids content is at least 60 percent by weight are especially useful since they exhibit increased stability and allow the formulator using the dispersions increased flexibility in formulation.

The invention is a dispersion of the fine particle sized zinc oxide dispersed in a high amount in an oil and is particularly directed to the use of an oil which is suitable for inclusion in a cosmetic product useful as a preparation to protect skin against sun-burning or other damage associated with exposure to ultra violet radiation. In particular the dispersions are useful in products designed to provide a balanced protection from both UVA radiation (wavelengths of 320–400 nm) and UVB radiation (wavelengths of 290–320 nm). Such materials are of increasing importance and use now since a greater number of people than ever are enjoying leisure activities in the outdoors and increasing their exposure to sunlight.

The particles of zinc oxide in the oil dispersion have an average size of from 0.005 to 0.15 micron and where the particles are substantially spherical then this size will be taken to represent the diameter. However since the invention also encompasses the use of non-spherical particles then in such cases the size refers to the largest dimension. Preferably the particles of zinc oxide have an average size within the range 0.01 to 0.1 micron and most preferably within the range 0.03 to 0.07 micron when they are substantially spherical in shape. For particles having an acicular shape then the average largest dimension preferably is within the range 0.05 to 0.12 micron.

The particles to be used to form the dispersions of the present invention may be uncoated or coated as is desired with one or more oxides or hydrous oxides of e.g. aluminium, silicon, titanium, zirconium, magnesium or zinc.

One preferred coating is formed of an oxide or hydrous oxide of aluminium and an oxide or hydrous oxide of silicon in a weight ratio of $Al_2O_3:SiO_2$ of at least 0.5 and not greater than 4.5 and preferably the ratio is within the range 0.5 to 3.5. Most preferably the ratio is within the range 1.0 to 3.5.

When such a coating containing aluminium and silicon oxides is employed then the actual amount of coating present is usually such that the amount of oxide or hydrous oxide of aluminium when expressed as $Al_2O_3$ is from 1.0 to 30.0 weight percent based on the weight of solid (zinc oxide), and preferably from 3.0 to 15.0 weight percent $Al_2O_3$ on weight of solid (zinc oxide). Consequently the amount of oxide or hydrous oxide of silicon will be that necessary to maintain the ratio of the amounts of coating oxides or hydrous oxides within the specified range and generally speaking the weight of oxide or hydrous oxide of silicon will be within the range 0.2 to 20.0 weight percent $SiO_2$ based on solid (zinc oxide) and preferably from 1.5 to 7.0 weight percent.

If desired the particulate material may carry a coating of one or more organic materials such as an organic silicon compound e.g. a polymeric organic silicon compound. Other organic coating agents which may be present are the polyols, amines or alkanolamines.

The particulate material of the present invention may be formed by any suitable process and typical processes are the French Method in which metallic zinc is melted and evaporated before being oxidized in the gas phase, the American method in which zinc ores are sintered and reduced with cokes and the zinc thus obtained is oxidised to zinc oxide and a wet method in which a water soluble zinc salt such as zinc chloride or zinc sulphate is crystallised and then converted to zinc oxide by sintering.

The products of the present invention have the ability to transmit visible light but are partially or completely impermeable to UV light. This means that the products can find use in a wide variety of applications wherein it is important to maintain transparency to visible light while substantially preventing transmission of UV light to a surface. Cosmetics, sun-creams, plastics films and wood coating and other coating compositions are just a small number of applications for the products.

The particle absorbancy for UV light is expressed as a function of the amount of the uncoated particle and when expressed as an extinction coefficient is substantially independent of the medium in which the particles are dispersed. The dispersion of particles of the present invention is partially or completely impermeable to a broad range of wavelengths of UV light and the extinction coefficients for UVA radiation (e.g. E(360)) and for UVB radiation (e.g. E(308)) are approximately equal. E(360) is greater than 9 liters per gram per centimeter and preferably greater than 10 liters per gram per centimeter. E(308) is greater than 9 liters per gram per centimeter and preferably both E(360) and E(308) are greater than 12 liters per gram per centimeter. Most preferably both E(360) and E(308) are between 12 and 30 liters per gram per centimeter. The ratio E(360-):E(308) is in the range 0.75:1 to 1.5:1 and, preferably, in the range 0.9:1 to 1.2:1.

The oil dispersions of the present invention are prepared by milling the zinc oxide product, coated or not, with a particulate grinding medium in the chosen oil and with a dispersing agent in the desired amount until the dispersion has the desired absorbance for ultraviolet light as hereinbefore described and the zinc oxide product has the particle size within the range stated hereinbefore.

The oil can be any oil which is desirably present in the resultant dispersion but usually will be an oil which finds value in a cosmetic preparation. Such oils usually are the vegetable oils, for example, fatty acid glycerides, fatty acid esters and fatty alcohols with typical examples being sunflower oil (fatty acid triglyceride), castor oil, oleic and linoleic glycerides, oleyl alcohol, isopropyl palmitate, pentaerythritol tetracaprylate/caprate, propylene glycol di-esters of coconut fatty acids and pentaerythritol tetraisostearate.

The mill which is employed to effect the grinding of the zinc oxide product in the oil is one which uses a particulate grinding medium to grind the product. Such mills are bead mills equipped with one or more agitators and using sand, glass beads, ceramic beads or other particles as the grinding medium.

Particularly useful are those mills which operate at a high speed and depending on the size of mill a speed of the order of 2500 rev per minute (r.p.m) is not unusual. For instance mills operating at a speed of from 1000 r.p.m. to 6000 r.p.m are suitable. Agitator mills in which the tip speed Of the agitator is up to and can exceed 10 meters/sec are of use. If desired the mill can be cooled. Also the ingredients of the dispersion can be pre-mixed using a high speed stirrer or the oil can be added to the mill initially and then the zinc oxide and the organic dispersant co-added to the oil subsequently. After milling has been carried out for the required time the dispersion is separated from the grinding medium by screening through a narrow gap.

The dispersions of the present invention include an organic dispersing agent to promote the dispersion of the particulate zinc oxide in the chosen oil. Many types of organic dispersing agent have been developed and are available for use in promoting the dispersion of particles in oily media. Typically the dispersing agent can be one having a formula X.CO.AR in which A is a divalent bridging group, R is a primary secondary or tertiary amino group or a salt thereof with an acid or a quaternary ammonium salt group and X is the residue of a polyester chain which together with the —CO— group is derived from a hydroxy carboxylic acid of the formula HO—R'—COOH. As examples of typical dispersing agents are those based on ricinoleic acid, hydroxystearic acid, hydrogenated castor oil fatty acid which contains in addition to 12-hydroxy-stearic acid small amounts of stearic acid and palmitic acid.

Dispersing agents which are polyesters or salts of one or more hydroxycarboxylic acid can also be used. These polyesters may also be formed from hydroxy carboxylic acids and carboxylic acids free from hydroxy groups. Compounds of various molecular weight can be used.

Other suitable dispersing agents are those monoesters of fatty acid alkanolamides and carboxylic acids and their salts based on 6–22C (un)saturated fatty acids.

Alkanolamides are based on ethanolamine, propanolamine or aminoethyl ethanolamine for example. Alternative dispersing agents are those based on polymers or copolymers of acrylic or methacrylic acids e.g. block copolymers of such monomers.

Other dispersing agents of similar general form are those having epoxy groups in the constituent radicals such as those based on the ethoxylated phosphate esters.

The dispersing agent can be one of those commercially referred to as a hyperdispersant specifically available as such and a particularly useful form of hyperdispersant is polyhydroxy stearic acid.

When the dispersions of the invention are to be used in cosmetic or skin care preparations then it is desirable that the ingredients should have an acceptable level of toxicity and irritancy.

The quantity of the dispersing agent used depends on various factors but generally an amount of from 5 percent to 35 percent, preferably 5 to 20 percent by weight based on the weight of zinc oxide particles will be used.

The invention is illustrated in the following Examples.

EXAMPLE 1

50 g uncoated spherical zinc oxide having an average particle size of 0.05 micron was added with 59.9 g of a mixture of equal parts by weight of a mineral oil sold under the Trade Name Ondina L and a triglyceride of caprylic/caprinic acid sold under the Trade Name Myritol 318 and 4.37 grams of a dispersant being a polyhydroxy stearic acid known as Solsperse 3000 to a high speed bead mill (Eiger M-50-VSE) with 60 grams of 1 mm glass beads as grinding aid. The dispersion was milled for 2 hours. The solids content of the dispersion was 43.8%, by weight.

After separation from the grinding aid a portion (0.1 gram) of the milled dispersion was diluted with n-hexane (100 ml). This diluted sample was then further diluted with n-hexane in the ratio sample:n-hexane of 1:19. The total dilution was 1:20,000.

The diluted sample was then exposed in a Perkin Elmer Lambda 2 spectrometer with a 1 cm path length and the absorbance of UV and visible light measured. Extinction coefficients at several wave lengths were calculated from the equation $A = E.c.l$ where $A$ = absorbance, $E$ = Extinction Coefficient in liters per gram per cm, $c$ = concentration in grams per liter and $l$ = path length in cm.

The absorbance of UV and visible light was measured as described above and the extinction coefficient at various wavelengths calculated as follows:

| E(308 nm) | E(360 nm) | E(524 nm) | E(max) | λ(max) |
|---|---|---|---|---|
| 12.7 | 12.7 | 0.6 | 13.0 | 364 |

EXAMPLE 2

175 g uncoated spherical zinc oxide having an average particle size of 0.05 micron was added with 249.4 g of a mixture of equal parts by weight of a mineral oil sold under the Trade Name Ondina L and a triglyceride of caprylic/caprinic acid sold under the Trade Name Myritol 318 and 13.1 g of a dispersant being a polyhydroxy stearic acid known as Solsperse 3000 to a high speed bead mill (Eiger M-250-VSE) with 200 g of 1 mm glass beads as grinding aid. The dispersion was milled for 45 minutes. The solids content of the dispersion was 40.0% by weight.

After separation from the grinding aid, a portion (0.02 g) of the milled dispersion was diluted with cyclohexane (100 ml). The total dilution was 1:5,000.

The diluted sample was then exposed in a Perkin Elmer Lambda 2 spectrometer as previously described in Example 1. The absorbance of UV and visible light was measured and the extinction coefficient at various wavelengths calculated as follows:

| E(308 nm) | E(360 nm) | E(524 nm) | E(max) | λ(max) |
|---|---|---|---|---|
| 11.5 | 11.5 | 0.6 | 11.6 | 362 |

EXAMPLE 3

200 g uncoated spherical zinc oxide having an average particle size of 0.05 micron was added with 185 g of a mixture of equal parts by weight of a mineral oil sold under the Trade Name Ondina L and a triglyceride of caprylic/caprinic acid sold under the Trade Name Myritol 318 and 15 g of a dispersant being a polyhydroxy stearic acid known as Solsperse 3000 to a high speed bead mill (Eiger M-250-VSE) with 200 g of 1 mm glass beads as grinding aid. The dispersion was milled for 45 minutes. The solids content of the dispersion was 50.0% by weight.

After separation from the grinding aid, a portion (0.02 g) of the milled dispersion was diluted with cyclohexane (100 ml). The total dilution was 1:5,000.

The diluted sample was then exposed in a Perkin Elmer Lambda 2 spectrometer as previously described. The absorbance of UV and visible light was measured and the extinction coefficient at various wavelengths calculated as follows:

| E(308 nm) | E(360 nm) | E(524 nm) | E(max) | λ(max) |
|---|---|---|---|---|
| 12.3 | 11.9 | 0.7 | 11.9 | 361 |

EXAMPLE 4

210 g uncoated spherical zinc oxide having an average particle size of 0.05 micron was added with 124.25 g of an octyl palmitate oil and 15.75 g of a dispersant being a polyhydroxy stearic acid known as Solsperse 3000 to a high speed bead mill (Eiger M-250-VSE) with 200 g of 1 mm glass beads as grinding aid. The dispersion was milled for 45 minutes. The solids content of the dispersion was 60.0% by weight.

After separation from the grinding aid, a portion (0.02 g) of the milled dispersion was diluted with cyclohexane (100 ml). The total dilution was 1:5,000.

The diluted sample was then exposed in a Perkin Elmer Lambda 2 spectrometer as previously described. The absorbance of UV and visible light was measured and the extinction coefficient at various wavelengths calculated as follows:

| E(308 nm) | E(360 nm) | E(524 nm) | E(max) | λ(max) |
|---|---|---|---|---|
| 12.8 | 12.3 | 0.5 | 12.3 | 361 |

EXAMPLE 5

210 g uncoated spherical zinc oxide having an average particle size of 0.05 micron was added with 124.25 g of a triglyceride of caprylic/caprinic acid sold under the Trade Name Myritol 318 and 15.75 g of a dispersant being a polyhydroxy stearic acid known as Solsperse 3000 to a high speed bead mill (Eiger M-250-VSE) with 200 g of 1 mm glass beads as grinding aid. The dispersion was milled for 45 minutes. The solids content of the dispersion was 60.0% by weight.

After separation from the grinding aid, a portion (0.02 g) of the milled dispersion was diluted with cyclohexane (100 ml). The total dilution was 1:5,000.

The diluted sample was then exposed in a Perkin Elmer Lambda 2 spectrometer as previously described. The absorbance of UV and visible light was measured and the extinction coefficient at various wavelengths calculated as follows:

| E(308 nm) | E(360 nm) | E(524 nm) | E(max) | λ(max) |
|---|---|---|---|---|
| 12.8 | 12.4 | 0.8 | 12.4 | 360 |

EXAMPLE 6

250 g of coated (2.0% $SiO_2$/8.0% $Al_2O_3$) spherical zinc oxide was added with 350 g of a mixture of equal parts by weight of a mineral oil sold under the Trade Name Ondina L and a triglyceride of caprylic/caprinic acid sold under the Trade Name Myritol 318 and 25 g of a dispersant being a polyhydroxy stearic acid known as Solsperse 3000 to a high speed bead mill (Eiger M-250-VSE) with 200 g of 1 mm glass beads as grinding aid. The dispersion was milled for 45 minutes. The solids content of the dispersion was 40.0% by weight.

After separation from the grinding aid, a portion (0.1 g) of the milled dispersion was diluted with cyclohexane (100 ml). This diluted sample was then further diluted with cyclohexane in the ratio sample:cyclohexane of 1:19. The total dilution was 1:20,000.

The diluted sample was then exposed in a Perkin Elmer Lambda 2 spectrometer as previously described. The absorbance of UV and visible light was measured and the extinction coefficient at various wavelengths calculated as follows:

| E(308 nm) | E(360 nm) | E(524 nm) |
|---|---|---|
| 10.6 | 9.5 | 2.7 |

I claim:

1. An oil dispersion comprising an oil, particles of zinc oxide having an average size of from 0.005 to 0.15 micron and an organic dispersing agent for said particles, the amount of said particles being such that the dispersion has a solids content of greater than 30 percent by weight and said dispersion being substantially transparent to visible light and having an absorbance for ultraviolet light such that the extinction coefficient (E(308)) at a wavelength of 308 nm is at least 9 liters per gram per centimeter, the extinction coefficient (E(360)) at a wavelength of 360 nm is at least 9 liters per gram per centimeter and the ratio E(360):E(308) is in the range 0.75:1 to 1.5:1.

2. An oil dispersion according to claim 1 in which the solids content is at least 40 percent by weight.

3. An oil dispersion according to claim 1 in which the solids content is at least 60 percent by weight.

4. An oil dispersion according to claim 1 in which the particles of zinc oxide are substantially spherical and have an average diameter within the range 0.01 to 0.1 micron.

5. An oil dispersion according to claim 4 in which the average diameter is within the range 0.03 to 0.07 micron.

6. An oil dispersion according to claim 1 in which the particles of zinc oxide are acicular and have an average largest dimension within the range 0.05 to 0.12 micron.

7. An oil dispersion according to claim 1 in which the extinction coefficient E(360) is greater than 10 liters per gram per centimeter.

8. An oil dispersion according to claim 1 in which both the extinction coefficients E(308) and E(360) are greater than 12 liters per gram per centimeter.

9. An oil dispersion according to claim 1 in which both the extinction coefficients E(360) and E(308) are between 12 and 30 liters per gram per centimeter.

10. An oil dispersion according to claim 1 in which the ratio E(360):E(308) is in the range 0.9:1 to 1.2:1.

11. An oil dispersion according to claim 1 in which the oil is selected from the group consisting of fatty acid glycerides, fatty acid esters and fatty alcohols.

12. An oil dispersion according to claim 1 in which the dispersing agent is based on an acid selected from the group consisting of ricinoleic acid, hydroxystearic acid and hydrogenated castor oil fatty acids.

13. An oil dispersion according to claim 1 in which the organic dispersing agent is selected from the group consisting of polyesters and salts of hydroxycarboxylic acids.

14. An oil dispersion according to claim 1 in which the organic dispersing agent is present in an amount of from 5 to 35 percent by weight with respect to zinc oxide.

15. An oil dispersion according to claim 14 in which the amount is from 5 to 20 percent by weight.

16. An oil dispersion according to claim 1 in which the particles of zinc oxide are coated with an oxide or hydrous oxide of a metal selected from the group consisting of aluminium, silicon, titanium, zirconium, magnesium and zinc.

17. An oil dispersion according to claim 16 in which the particles of zinc oxide are coated with an oxide or hydrous oxide of aluminium and an oxide or hydrous oxide of silicon in a weight ratio of $Al_2O_3:SiO_2$ between 0.5 and 4.5.

18. An oil dispersion according to claim 17 in which the weight ratio is between 0.5 and 3.5.

19. An oil dispersion according to claim 17 in which the weight ratio is between 1.0 and 3.5.

20. An oil dispersion according to claim 17 in which the amount of oxide or hydrous oxide of aluminium, expressed as $Al_2O_3$, is from 1.0 to 30.0 weight percent based on weight of zinc oxide.

21. An oil dispersion according to claim 20 in which the amount of oxide or hydrous oxide of aluminium is from 3.0 to 15.0 weight percent based on zinc oxide.

22. An oil dispersion according to claim 17 in which the amount of oxide or hydrous oxide of silicon, expressed as $SiO_2$, is from 0.2 to 20.0 weight percent based on zinc oxide.

23. An oil dispersion according to claim 22 in which the amount of oxide or hydrous oxide of silicon is from 1.5 to 7.0 weight percent based on zinc oxide.

24. An oil dispersion according to claim 1 in which the particles of zinc oxide are coated with an organic material.

25. An oil dispersion according to claim 24 in which the organic material is selected from the group consisting of organic silicon compounds, polyols, amines and alkanolamines.

26. A method for the manufacture of an oil dispersion comprising milling particulate zinc oxide in an oil in the presence of a particulate grinding medium and an organic dispersing agent for said zinc oxide in said oil in which the amount of zinc oxide is such that the dispersion has a solids content of greater than 30 percent by weight and continuing said milling for a period of time such that the particulate zinc oxide has an average size of from 0.005 to 0.15 micron and that the dispersion obtained is substantially transparent to visible light and has an absorbance for ultraviolet light such that the extinction coefficient (E(308)) at a wavelength of 308 nm is at least 9 liters per gram per centimeter, the extinction coefficient (E(360)) at a wavelength of 360 nm is at least 9 liters per gram per centimeter and the ratio E(360):E(308) is in the range 0.75:1 to 1.5:1.

27. A method according to claim 26 in which the particulate grinding medium is selected from the group consisting of sand, glass beads and ceramic beads.

28. A method according to claim 26 in which the particulate zinc oxide is milled in a mill operating at a speed of from 1000 to 6000 revolutions per minute.

29. A method according to claim 26 in which the zinc oxide, oil and organic dispersing agent are mixed using a high speed stirrer before being added to a mill.

* * * * *

(12) EX PARTE REEXAMINATION CERTIFICATE (8339th)
United States Patent
Tapley

(10) Number: US 5,366,660 C1
(45) Certificate Issued: Jun. 28, 2011

(54) DISPERSIONS

(75) Inventor: Carole A. M. Tapley, Stockton on Tees (GB)

(73) Assignee: Uniqema Americas LLC

Reexamination Request:
No. 90/010,376, Dec. 31, 2008

Reexamination Certificate for:
Patent No.: 5,366,660
Issued: Nov. 22, 1994
Appl. No.: 07/953,219
Filed: Sep. 30, 1992

(30) Foreign Application Priority Data

Oct. 4, 1991 (GB) .............................................. 9121143

(51) Int. Cl.
*A61K 8/00* (2006.01)
*A61K 8/27* (2006.01)
*A61K 8/34* (2006.01)
*A61K 8/36* (2006.01)
*A61K 8/365* (2006.01)
*A61K 8/37* (2006.01)
*A61K 8/85* (2006.01)
*A61K 8/92* (2006.01)
*A61Q 17/04* (2006.01)
*B01J 2/00* (2006.01)
*B01J 13/00* (2006.01)
*B01J 19/00* (2006.01)
*B02C 17/00* (2006.01)
*B02C 19/00* (2006.01)
*C01G 9/02* (2006.01)
*C01G 9/00* (2006.01)
*C09C 1/04* (2006.01)
*C09D 5/32* (2006.01)
*G02B 5/23* (2006.01)
*G02B 5/22* (2006.01)

(52) U.S. Cl. ............................ 516/33; 106/425; 106/426; 252/588; 424/59; 423/622; 516/34; 516/922; 516/930

(58) Field of Classification Search ........................ None
See application file for complete search history.

(56) References Cited

U.S. PATENT DOCUMENTS

| 4,882,143 A | 11/1989 | Kadokura |
| 5,028,417 A | 7/1991 | Bhat |
| 5,032,390 A | 7/1991 | Iwaya |
| 5,143,722 A | 9/1992 | Hollenberg |
| 5,340,567 A | 8/1994 | Cole |
| 5,599,529 A | 2/1997 | Cowie |

FOREIGN PATENT DOCUMENTS

| CA | 2032201 AA | 6/1991 |
| GB | 1373660 A | 11/1974 |
| JP | 60-231607 A2 | 11/1985 |
| JP | 3-183620 A2 | 8/1991 |

*Primary Examiner*—Evelyn Huang

(57) ABSTRACT

An oil dispersion which is substantially transparent to visible light comprises an oil, particles of zinc oxide having an average size of from 0.005 to 0.15 micron and an organic dispersing agent. The solids content of the dispersion is at least 30 weight percent, its extinction coefficients at 308 nm (E(308)) and 360 nm (E(360)) wavelengths are both at least 9 liters per gram per centimeter and the ratio E(360):E(308) is in the range 0.75:1 to 1.5:1.

A method of preparing the dispersion is also described in which the ingredients are milled together in the presence of a particulate grinding medium until the required particle size and optical properties are obtained.

The dispersions are useful in sun-screening preparations and especially those products designed to provide a balanced protection from UVA and UVB radiation.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-29 are cancelled.

* * * * *